United States Patent [19]

Kleiner et al.

[11] Patent Number: 4,670,601
[45] Date of Patent: Jun. 2, 1987

[54] PROCESS FOR THE PREPARATION OF BIFUNCTIONAL TERTIARY AROMATIC PHOSPHINE SULFIDES

[75] Inventors: Hans-Jerg Kleiner, Kronberg; Erwin Weiss, Hofheim am Taunus, both of Fed. Rep. of Germany

[73] Assignee: Hoechst Aktiengesellschaft, Frankfurt am Main, Fed. Rep. of Germany

[21] Appl. No.: 756,326

[22] Filed: Jul. 18, 1985

[30] Foreign Application Priority Data

Jul. 20, 1984 [DE] Fed. Rep. of Germany ....... 3426722

[51] Int. Cl.⁴ ................................................ C07F 9/53
[52] U.S. Cl. ..................................................... 568/14
[58] Field of Search .......................................... 568/14

[56] References Cited

U.S. PATENT DOCUMENTS

| | | | |
|---|---|---|---|
| 3,105,097 | 9/1963 | Willans | 568/14 |
| 3,305,589 | 2/1967 | Bacon | 568/14 |
| 3,988,368 | 10/1976 | Ura et al. | 568/14 X |
| 4,052,463 | 10/1977 | Uhing et al. | 568/14 |
| 4,101,655 | 7/1978 | Sukman . | |

FOREIGN PATENT DOCUMENTS

| | | | |
|---|---|---|---|
| 571317 | 2/1959 | Canada | 568/14 |
| 1238024 | 6/1964 | Fed. Rep. of Germany . | |
| 2743848 | 8/1977 | Fed. Rep. of Germany . | |

OTHER PUBLICATIONS

Kosolapoff, Organic Phosphorus Compounds Wiley-Intersc. N.Y., vol. 4, pp. 15 and 16 (1972).
Helvetica Chimica Acta 47, pp. 120 to 132 (1964).
Olah et al., J. Org. Chem., 42, No. 12, 2190 (1977).

*Primary Examiner*—Helen M. S. Sneed
*Attorney, Agent, or Firm*—Curtis, Morris & Safford

[57] ABSTRACT

Tertiary aromatic phosphine sulfides of the formula

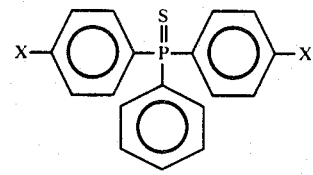

wherein X=F, Cl or Br, are prepared by means of a Friedel-Crafts reaction of
(a) $PCl_3$ with benzene and—after the addition of sulfur—also with fluorobenzene, chlorobenzene or bromobenzene, or
(b) $PSCl_3$ with fluorobenzene, chlorobenzene or bromobenzene and subsequently also with benzene; Friedel-Crafts catalysts are Al halides, especially $AlCl_3$.

The products are used as end products and intermediates in a variety of areas, such as, for example, the sectors of plant protection and polymers.

17 Claims, No Drawings

PROCESS FOR THE PREPARATION OF BIFUNCTIONAL TERTIARY AROMATIC PHOSPHINE SULFIDES

Bifunctional tertiary aromatic phosphine sulfides are inter alia the bis(4-halogenophenyl)phenylphosphine sulfides of the formula

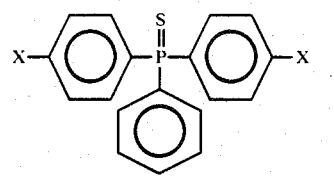

wherein X=halogen.

They are valuable end products and intermediates in a variety of areas.

Bis(4-halogenophenyl)phenylphosphine sulfides (and oxides) are end products in, for example, the plant protection sector as insecticides and acaricides (German Offenlegungsschrift No. 27 43 848=U.S. Pat. No. 4,101,655).

The compounds are intermediates in, for example, the polymer sector. To be used in this area, the compounds must first be converted (by an oxidative route) to the corresponding phosphine oxides, which can then be condensed with certain bisphenols to give valuable polymers (German Offenlegungsschrift 32 03 186), for example:

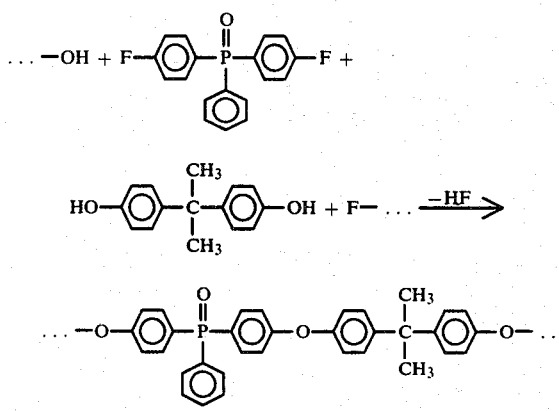

The polymers are distinguished by a particularly low combustibility and extreme thermal stability; they can be processed to fibers, films and moldings etc.

As indicated in the abovementioned German Offenlegungsschrift 27 43 848, the bis(4-halogenophenyl)-phenylphosphine sulfides can be prepared for example by means of a Grignard reaction between dichlorophenylphosphine and halogenophenylmagnesium halide and subsequent reaction with elemental sulfur, according to the (schematic) equations below:

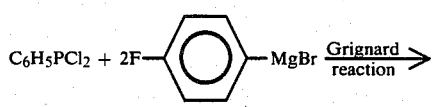

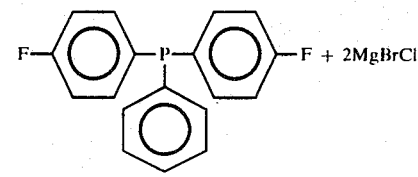

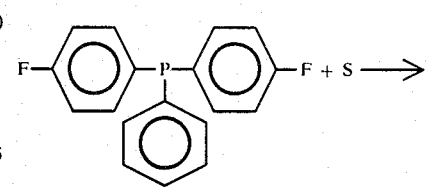

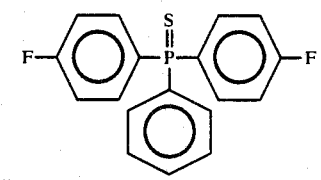

If hydrogen peroxide, $H_2O_2$, is used in the second reaction step in place of the elemental sulfur, the corresponding phosphine oxides are obtained directly:

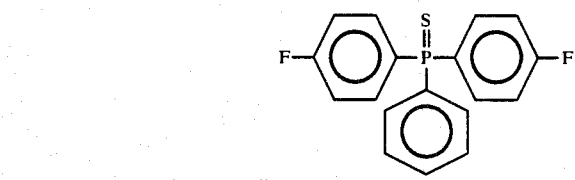

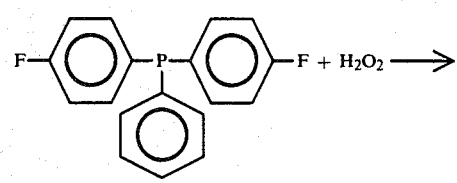

The phosphine oxides can alternatively be obtained also by means of a Grignard reaction between phenylphosphonic acid dichloride and halogenophenylmagnesium halide:

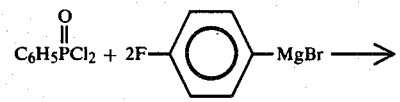

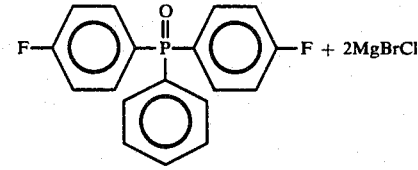

Finally, arylated thiophosphorus compounds, for example bis(4-halogenophenyl)phenylphosphine sulfides, can also be prepared by the process of German Patent No. 1 238 024, which comprises a Friedel-Crafts reaction between thiophosphorus halide compounds, for example phenylthiophosphonic acid dichloride, $C_6H_5P(S)Cl_2$, and aromatic compounds, for example halogenobenzenes, in the presence of at least an equimolar quantity of a Friedel-Crafts catalyst (especially $AlCl_3$), based on the thiophosphorus halide compound, and with at least an equimolar quantity of the aromatic compounds, based on the halogen atoms to be replaced, with subsequent decomposition of the resulting catalyst complex with water or ice or in a manner known per se by the addition of a compound which forms a stronger complex with the catalyst than does the thiophosphorus compound to be isolated. For the preparation of bis(4-fluorophenyl)phenylphosphine sulfide, for example, by this process, the corresponding equation would be:

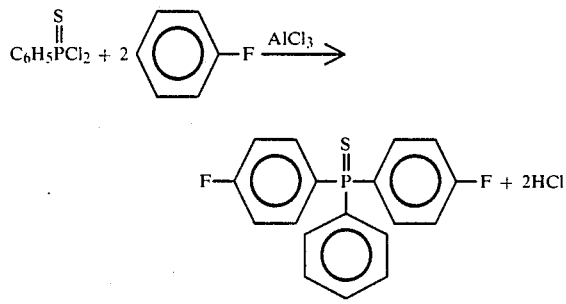

However, the preparation of this compound and also of other bis(4-halogenophenyl)phenylphosphine sulfides is not covered by examples in the said German patent. The only examples relating to reaction with a halogenobenzene are Examples 7, 8 and 9 (reaction of $PSCl_3$ with chlorobenzene) and 15 and 16 (reaction of $PSCl_3$ with fluorobenzene).

According to Example 7, phosphorus thiochloride, $PSCl_3$, $AlCl_3$ and chlorobenzene, $C_6H_5Cl$, are heated under reflux for 7 hours in a molar ratio of 1:5.33:6.67. The yield of tris(chlorophenyl)phosphine sulfide, $PS(C_6H_4Cl)_3$, based on $PSCl_3$ used, is given as 64%; the product is said to consist of approximately equal parts of the o and p isomers according to the IR spectrum.

In Example 8, the molar ratio of $PSCl_3$:$AlCl_3$:$C_6H_5Cl$ is 1:2:4. After heating under reflux for 1¼ hours, the following are said to have been obtained: 63.2% of bis(chlorophenyl)thiophosphinic acid chloride, $(C_6H_4Cl)_2P(S)Cl$ (after recrystallization), together with a significant quantity of a residue said to have consisted of a mixture of isomeric tris(chlorophenyl)phosphine sulfides, $(C_6H_4Cl)_3PS$.

In Example 9, the ratio of $PSCl_3$:$AlCl_3$: $C_6H_5Cl$ was 1:2.5:1. After heating under reflux for one hour, the following are said to have been obtained:
45.4% of chlorophenylthiophosphonic acid dichloride, $(C_6H_4Cl)P(S)Cl_2$,
19.7% of bis(chlorophenyl)thiophosphinic acid chloride, $(C_6H_4Cl)_2P(S)Cl$, as a mixture of isomers, and
18.3% of tris(chlorophenyl)phosphine sulfide, $(C_6H_4Cl)_3P(S)$.

Mixtures of isomers are only mentioned for the product of Example 7, the residue of Example 8 and the middle fraction of Example 9. It is hardly conceivable, however, that the other chlorophenyl products were free of isomers. All reaction products are therefore presumably appropriate mixtures of isomers.

According to Example 15, $PSCl_3$, $AlCl_3$ and fluorobenzene, $C_6H_5F$, were heated under reflux for 4 hours in a molar ratio of 1:5.33:6.67. 79.5% of bis(4-fluorophenyl)thiophosphinic acid chloride, $(C_6H_4F)_2P(S)Cl$ virtually free of isomers, is said to have been obtained together with only a trace of the o isomer and an insignificant residue.

In Example 16, the molar ratio of $PSCl_3$:$AlCl_3$: $C_6H_5F$ was 1:2.2:1.1. The result after heating under reflux for 1¾ hours was as follows:
23.2% of virtually pure fluorophenylthiophosphonic acid dichloride, $(C_6H_4F)P(S)Cl_2$,
14.2% of bis(fluorophenyl)thiophosphinic acid chloride, $(C_6H_4F)_2P(S)Cl$ (with no information on the isomeric purity), and
a quite significant quantity of a brown residue.

In order to obtain the bis(4-halogenophenyl)phenyl phosphine sulfides from the bis(4-halogenophenyl)thiophosphinic acid chlorides obtained in varying yields according to these examples, the bis(4-halogenophenyl)thiophosphinic acid chlorides would presumably have to be subjected to a further Friedel-Crafts reaction with benzene, after their isolation and, if appropriate, separation of the isomers.

The phosphine oxides required for the polymer sector could then be obtained from the phosphine sulfides, for example by reaction with $SOCl_2$ or with oxidizing agents such as $KMnO_4$; cf., for instance, the article by L. Maier—also the inventor of the abovementioned German Patent 1 238 024—in Helvetica Chimica Acta 47, pages 120-132, especially page 124 (1964). Particularly advantageously, tertiary phosphine sulfides can also be converted to the corresponding phosphine oxides by the process according to Patent Application HOE 84/F 162, filed simultaneously, using $H_2O_2$ in a solvent consisting of at least about 20% by weight of lower aliphatic carboxylic acids and/or their anhydrides (remainder: other inert solvents).

The route via the tertiary aromatic phosphine sulfides to the corresponding phosphine oxides is necessary here because the Friedel-Crafts reaction of $POCl_3$ with benzene and halogenoaromatics is virtually never successful.

The known processes for the preparation of bis (4-halogenophenyl)phenylphosphine sulfides are unsatisfactory or not totally satisfactory in various respects, especially for industrial requirements. The abovementioned Grignard reaction starting from dichlorophenylphosphine, or phenylphosphonic acid dichloride, and halogenophenylmagnesium halide cannot be carried out in a totally straightforward manner on the industrial scale.

The Friedel-Crafts reaction according to German Patent No. 12 38 024, starting from $PSCl_3$ and halogenobenzene, leads—as shown by Examples 7 to 9—to yields of at most only about 63% (Example 8) of a mixture of isomers consisting of bis(4-chlorophenyl)thiophosphinic acid chloride and bis(2-chlorophenyl)thiophosphinic acid chloride—presumably in approximately equal parts—at any rate in cases where chlorobenzene is used as the halogenobenzene. The bis(4-chlorophenyl)thiophosphinic acid chloride is only the precursor of the bis(4-chlorophenyl)phenylphosphine sulfide which is desired for the polymer sector.

The problem was therefore to find an improved process for the preparation of bis(4-halogenophenyl)phenylphosphine sulfides.

It was possible to solve this problem, according to the invention, by developing the process described in German Patent No. 12 38 024.

The invention therefore relates to a process for the preparation of tertiary aromatic phosphine sulfides of the formula

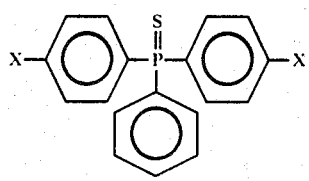

wherein X=F, Cl or Br, by means of a Friedel-Crafts reaction of P-Cl compounds with benzene and a halogenobenzene; in this process, (a) phosphorus trichloride, $PCl_3$, is heated with an aluminum halide and benzene in a molar ratio of 1:approx. 1 to 3.5:approx. 1 until the reaction has ended, and then, without isolation of an intermediate and after the addition of an equimolar quantity—relative to $PCl_3$—of elemental sulfur and of an approximately 2-fold to 10-fold molar quantity of halogenobenzene of the formula $C_6H_5X$, wherein X has the abovementioned meaning, the mixture is heated again until the reaction has ended, if appropriate with the addition of a further quantity of aluminum halide (if a molar ratio of $PCl_3$:Al halide=1: approx. 2-3.5 has not already been used at the outset), and the reaction product is worked up in the usual manner, or (b) phosphorus thiochloride, $PSCl_3$, aluminum halide and a halogenobenzene of the formula $C_6H_5X$, wherein X has the abovementioned meaning, are heated in a molar ratio of 1: approx. 1-3.5:2 until the reaction has ended, and then, without isolation of an intermediate and after the addition of an approximately 1-fold to 10-fold molar quantity—relative to $PSCl_3$—of benzene, the mixture is again heated until the reaction has ended, and the reaction mixture is worked up in the usual manner.

Reactions (a) and (b) are based on the following equations:

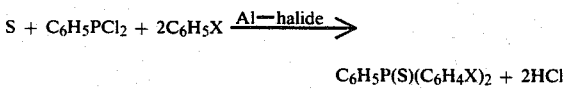

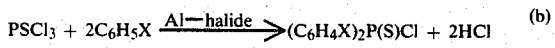

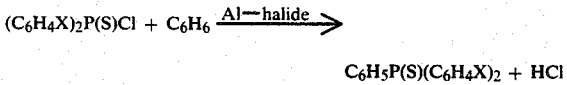

In this process (both in variant a) and in variant b)), the bis(4-halogenophenyl)phenylphosphine sulfides are obtained as by far the predominant products—i.e. in every case in yields of between about 65 and 75% of theory, based on the starting $PCl_3$ or $P(S)Cl_3$—together with only a relatively small quantity of isomers and other by-products, in a kind of one-pot reaction (since no intermediate is isolated). This result is particularly surprising because each of the two variants (a) and (b), which in turn consists of two partial reactions in each case, produces, at any rate in the case of reaction with chlorobenzene, a yield of the end product, bis(4-halogenophenyl)phenylphosphine sulfide, which is virtually twice as high as the yield of the intermediate, bis(4-chlorophenyl)phosphinic acid chloride, produced in the process according to German Patent No. 12 38 024. The most favorable example in this German patent (Example 8), relating to the reaction with chlorobenzene to give the said phosphinic acid chloride, produces—as mentioned in the introductory description of the state of the art—a yield of 63.2% of what can be concluded from the other statements in this German patent to be a mixture of approximately equal parts of the o and p isomers, which means a yield of the p isomer, namely bis(4-chlorophenyl)-thiophosphinic acid chloride, of about 30 to 35%.

Example 15 of German Patent No. 1 238 024 furthermore shows that bis(4-fluorophenyl)thiophosphinic acid chloride is obviously only formed in good yields when using excesses of fluorobenzene above the theoretical quantity of 2 moles of fluorobenzene/mole of phosphorus thiochloride. However, since virtually no tertiary phosphine sulfides are formed when using excesses (1:6.67 moles) in this example, it was to be expected that bis(4-fluorophenyl)thiophosphinic acid chloride would also form virtually no tertiary phosphine sulfide with benzene (optionally in excess), because, according to L. Maier (loc. cit.), fluorobenzene reacts in the same way as benzene in the presence of Al halides.

$AlCl_3$, $AlBr_3$ and alkylaluminum chloride and bromide are preferably used as aluminum halides for the process according to the invention; $AlCl_3$ is particularly preferred as the aluminum halide.

Suitable halogenobenzenes $C_6H_5X$ are fluorobenzene, chlorobenzene and bromobenzene, preference being given to fluorobenzene and chlorobenzene.

To carry out variant (a) of the process according to the invention, $PCl_3$, the Al halide and benzene are brought together in a suitable vessel, the molar ratio of the said 3 reactants generally being 1: approx. 1 to 3.5 (preferably 1 to 2.5) : approx. 1. In principle, it is also possible to use excess $PCl_3$, but this must then be removed again (preferably by distillation) after the reaction has ended. It is also possible, although not advantageous, to use excesses of Al halide. The reactants are then heated— preferably under reflux—until the reaction has ended. The reaction temperature is generally between about 7° and 100° C. and the reaction time between about 3 and 12 hours.

It is advantageous for the heating to be carried out under an inert gas atmosphere (for example nitrogen or argon).

After the 1st reaction step has ended, the reaction mixture is advantageously cooled. It is then treated, without isolation of an intermediate, with 1 mole of sulfur and about 2 to 10 moles of halogenobenzene, based in each case on the $PCl_3$ converted. It is preferable to use about 3 to 6 moles in the case of fluorobenzene and about 6 to 8 moles in the case of chlorobenzene and bromobenzene.

It necessary to add Al halide in this step if less than 2 moles/mole of $PCl_3$ converted have been used in the first step. However, a quantity of Al halide larger than about 3.5 moles, based on the $PCl_3$ (converted), is not advantageous.

The mixing to prepare the second reaction step is advantageously carried out with cooling. The reaction mixture prepared in this way is then heated again, as a rule under reflux, until the reaction has ended, during which time the temperatures should not as far as possible exceed about 150° C. (if chlorobenzene and bromobenzene are used) or about 120° C. (if fluorobenzene is used). The reaction time here is normally between about 5 and 20 hours.

Variant (b) of the process according to the invention starts from $PSCl_3$ or an equimolar mixture of $PCl_3$ and elemental sulfur (which gives $PSCl_3$ in the presence of Al halide), Al halide and fluorobenzene, chlorobenzene or bromobenzene in a molar ratio normally of 1 : approx. 1 to 3.5 : 2. Here again, an excess of Al halide is possible in principle, although not advantageous. The reactants are mixed and heated until the reaction has ended. The reaction temperature should not exceed about 150° C. if chlorobenzene and bromobenzene are used and about 120° C. if fluorobenzene is used. The reaction time here is generally about 1 to 10 hours. This reaction is also advantageously carried out under an inert gas atmosphere (nitrogen, argon etc.).

After the first reaction step has ended, the mixture is advantageously cooled and, without isolation of an intermediate, treated with about 1 to 10 moles, preferably about 3 to 6 moles, of benzene, based on the starting $PSCl_3$, and if appropriate with Al halide. The addition of further Al halide is necessary if less than 2 moles/mole of $PSCl_3$ has been used in the first reaction step. The total quantity of Al halide used (in both reaction steps) should not be substantially more than about 3.5 moles/mole of $PSCl_3$. The reaction mixture is then preferably heated under reflux again until the reaction has ended. The reaction time here is normally between about 8 and 20 hours.

Completion of the individual partial reactions, both in variant (a) and in variant (b) of the process according to the invention, can be detected, for example, by the cessation of the evolution of hydrogen chloride (see the equations) or by following the course of the reaction in a customary manner (for example using chromatographic methods).

In both reaction steps of the two variants (a) and (b) of the process according to the invention, it is also possible to use inert solvents—especially for the purpose of regulating the reaction temperature when heating under reflux. Possible examples of such inert solvents are: aliphatic hydrocarbons such as petroleum ether, hexane and octane; cycloaliphatic hydrocarbons such as cyclohexane; hydroaromatic compounds such as decalin; etc.

In principle, the working-up of the reaction products obtained by the two variants a) and b) is carried out in the same way by known methods. To do this, the resulting reaction mixtures are decomposed with excess water or an aqueous mineral acid (for example hydrochloric acid), advantageously with cooling. To improve the phase separation, it is possible to add a suitable inert organic solvent—if this is not already present—the inert solvents mentioned above also being suitable for this purpose. If solvent or excess halogenobenzene or benzene is to be separated off, the whole organic phase is subjected to distillation after drying. The resulting distillation residues are essentially the desired bis(4-halogenophenyl)phenylphosphine sulfides in crude form. They are purified in a manner known per se, advantageously by distillation or recrystallization. The thiophosphinic acid halides (arising from incomplete conversions), which can readily be separated off by distillation, can be recycled into repeat reactions. This permits a further increase in the total yield, which would otherwise be between about 65 and 75% of theory, based on the starting P compound (converted).

The examples which follow are now intended to illustrate the invention in greater detail.

Variant (a)

EXAMPLE 1

Bis(4-chlorophenyl)phenylphosphine sulfide 13.73 g (0.1 mole) of phosphorus trichloride, 29.3 g (0.22 mole) of aluminum chloride and 7.81 g (0.1 mole) of benzene (molar ratio =1:2.2:1) were mixed in a nitrogen atmosphere, with stirring. The mixture was then heated to 80° C., a small quantity of hydrogen chloride being evolved. When the evolution of hydrogen chloride had ended after 6 hours, the mixture was cooled.

3.2 g (0.1 mole) of sulfur and 67.54 g (0.6 mole) of chlorobenzene were then added to the reaction mixture, which was boiled under reflux for a further 6 hours. The final reaction temperature was approx. 14° C. The initially vigorous evolution of hydrogen chloride had ceased almost completely. The mixture was then cooled and poured onto ice. The phases were separated and the aqueous phase rinsed again with chlorobenzene. After drying over sodium sulfate, the combined organic phases were filtered and the solvent was distilled off at 75° C./0.1 mbar. The residue consisted of 31.2 g (approx. 86% of theory) of crude bis(chlorophenyl)phenylphosphine sulfide, which crystallized substantially in the course of a few weeks.

According to $_{31}P$-NMR and GC analysis, the crude product consisted of approx. 76% of bis(4-chlorophenyl)phenylphosphine sulfide, 8% of isomeric bis(chlorophenyl)phenylphosphine sulfides, 6% of phenyl(4-chlorophenyl)thiophosphinic acid chloride, 6% of diphenyl(4-chlorophenyl)phosphine sulfide and 2.5% of tris(4-chlorophenyl)phenylphosphine sulfide.

Based on the starting $PCl_3$, this represents: approx. 65% of bis(4-chlorophenyl)phenylphosphine sulfide, approx. 7% of isomeric bis(chlorophenyl)phenylphosphine sulfides, approx. 5% of phenyl(4-chlorophenyl)thiophosphinic acid chloride, approx. 5% of diphenyl(4-chlorophenyl)phosphine sulfide and approx. 2% of tris(4-chlorophenyl)phenylphosphine sulfide.

EXAMPLE 2

Bis(4-fluorophenyl)phenylphosphine sulfide and oxide 13.73 g (0.1 mole) of phosphorus trichloride, 29.3 g (0.22 mole) of aluminum chloride and 7.81 g (0.1 mole) of benzene (molar ratio =1:2.2:1) were heated at 80° C. for 6 hours.

After the addition of 3.2 g (0.1 mole) of sulfur and 57.66 g (0.6 mole) of fluorobenzene, the mixture was boiled under reflux for 10 hours, poured onto ice and extracted by shaking with methylene chloride.

The organic phase was concentrated in a rotary evaporator and the crude phosphine sulfide was converted to the phosphine oxide by the process of patent application HOE 84/F 162, filed simultaneously. To do this, the crude phosphine sulfide was taken up in 100 ml of glacial acetic acid, and 10 ml of a 35% hydrogen peroxide solution were added dropwise at 50° C. over a period of ½ hour (with cooling). The mixture was subsequently 10 stirred for 30 minutes and cooled to 20° C., the sulfur was filtered off and the filtrate was evaporated at 100° C./20 mbar. The residue was suspended in 100 ml of water, the suspension was rendered alkaline with 2 N NaOH and the crude phosphine oxide was filtered off. Distillation in a bulb tube at 225° C./0.1 mbar gave 23.15 g ≐74% of theory, based on PCl₃ of a product having the following composition: 87.5% of bis(4-fluorophenyl)phenylphosphine oxide, 3.6% of diphenyl(4-fluorophenyl)phosphine oxide, 6.3% of tris(4-fluorophenyl)phenylphosphine oxide and 3.6% of other compounds (unknown).

Based on the starting PCl₃, this represents: approx. 65% of bis(4-fluorophenyl)phenylphosphine oxide, approx. 2% of diphenyl(4-fluorophenyl)phosphine oxide, approx. 5% of tris(4-fluorophenyl)phenylphosphine oxide and approx. 2.5% of other compounds (unknown).

Variant(b)

EXAMPLE 3

Bis(4-fluorophenyl)phenylphosphine sulfide

A mixture of 16.94 g (0.1 mole) of thiophosphoric acid trichloride, PSCl₃, 14.0 g (0.105 mole) of aluminum chloride and 19.22 g (0.2 mole) of fluorobenzene (molar ratio=1:1.05:2) was heated at 100° C. (oil bath temperature) for 6 hours using a reflux condenser cooled with iced water.

A further 19.3 g (0.145 mole) of aluminum chloride and 31.2 g (0.40 mole) of benzene were then added and the reaction mixture was boiled under reflux for 10 hours, cooled and poured onto ice.

The aqueous phase was carefully decanted and rinsed again with methylene chloride. The combined organic phases were dried over Na₂SO₄, the solvent was distilled off and the residue was distilled in vacuo.

The first runnings contained almost exclusively bis(4-fluorophenyl)thiophosphinic acid chloride (4 g), which can be recycled.

The residue was then distilled in a bulb tube (oven temperature =225° C./0.1 mbar). This gave 25.2 g (76.3% of theory) of volatile products which, on the basis of ³¹P-NMR analysis, consisted of the following products: 93.3% of bis(4-fluorophenyl)phenylphosphine sulfide, 4.33% of diphenyl(4-fluorophenyl)phosphine sulfide, 1.38% of triphenylphosphine sulfide and 0.99% of other compounds (unknown).

Based on the starting PSCl₃, this represents: approx. 71% of bis(4-fluorophenyl)phenylphosphine sulfide, approx. 3.3% of diphenyl(4-fluorophenyl)phosphine sulfide, approx. 1% of triphenylphosphine sulfide and approx. 0.75% of other compounds (unknown).

If the product in the first runnings, i.e. bis(4-fluorophenyl)thiophosphinic acid chloride, is recycled (added after the first reaction step), the yield increases somewhat.

EXAMPLE 4

Bis(4-chlorophenyl)phenylphosphine sulfide

A mixture of 16.94 g (0.1 mole) of phosphorus thiochloride, 33.34 g (0.25 mole) of aluminum chloride and 22.51 g (0.2 mole) of chlorobenzene (molar ratio =1:2.5:1) was heated at 130° C. (oil bath temperature) for 2 hours under an N₂ atmosphere. After cooling, 31.2 g (0.4 mole) of benzene were added and the mixture was boiled under reflux for 10 hours. It was poured onto ice and the phases were separated after the addition of methylene chloride. After drying over sodium sulfate, filtration and stripping of the solvent in vacuo (75° C./0.1 mbar), the residue consisted of 33.8 g of crude bis(4-chlorophenyl)phenylphosphine sulfide. This corresponds to a yield of 93% of theory (based on phosphorus thiochloride). The product crystallized almost completely in the course of a few days.

Crystallization from glacial acetic acid gave 25.5 g (70.2% of theory, based on PSCl₃) of bis(4-chlorophenyl)phenylphosphine sulfide.

EXAMPLE 5

A reaction completely analogous to Example 4 was carried out and the resulting crude product (prior to crystallization from glacial acetic acid) was subjected to distillation in a bulb tube (oven temperature =250° C./0.1 mbar). This gave 30.5 g (84.0% of theory) of volatile products which, according to ³¹P-NMR and GC analysis, had the following composition: 79.3% of bis(4-chlorophenyl)phenylphosphine sulfide, 10.2% of isomeric bis(chlorophenyl)phenylphosphine sulfides, 6.0% of bis(4-chlorophenyl)thiophosphinic acid chloride, 2.6% of diphenyl(4-chlorophenyl)phosphine sulfide, 0.6% of tris(4-chlorophenyl)phosphine sulfide and 1.3% of unknown compounds.

Based on the starting PSCl₃, this represents: approx. 67% of bis(4-chlorophenyl)phenylphosphine sulfide, approx. 8.5% of isomeric bis(chlorophenyl)phenylphosphine sulfides, approx. 5% of bis(4-chlorophenyl)thiophosphinic acid chloride, approx. 2.2% of diphenyl(4-chlorophenyl)phosphine sulfide, approx. 0.5% of tris(4-chlorophenyl)phosphine sulfide and approx. 1% of other compounds.

EXAMPLE 6

A third reaction was carried out in such a way that the phosphorus thiochloride was replaced with an equivalent quantity of phosphorus trichloride and sulfur.

13.73 g (0.1 mole) of PCl₃, 3.02 g (0.1 mole) of sulfur, 33.34 g (0.25 mole) of aluminum chloride and 22.51 g (0.2 mole) of chlorobenzene were mixed. After the spontaneous heating had died down, the mixture was heated for a further 2 hours at 130° C. and cooled to some extent, 31.2 g (0.4 mole) of benzene were added and the mixture was boiled under reflux for 10 hours. Working-up was carried out as in Example 4.

This gave 24.2 g (66.6% of theory, based on PCl₃) of crude bis(chlorophenyl)phenylphosphine sulfide.

We claim:

1. A process for the preparation of a bis(4-halogenophenyl)phenylphosphine sulfide of the formula

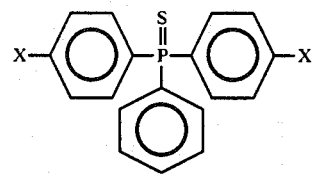

wherein X is F, Cl or Br, comprising heating a reaction mixture of phosphorous trichloride, an aluminum halide and benzene in a molar ratio of 1: approximately 1 to 3.5: approximately 1 and then, without isolation of an intermediate, adding to the reaction mixture an equimolar quantity of sulfur, relative to the phosphorous trichloride, an approximately two- to ten-fold molar quantity of a halogenobenzene of the formula C₆H₅X, wherein X has the above-mentioned meaning and an amount of aluminum halide so that the molar ratio in the reaction mixture of aluminum halide: phosphorous trichloride converted in said first heating step is 1: approximately 2 to 3.5, and heating the reaction mixture again until the reaction is complete to form the bis(4-halogenophenyl)phenylphosphine sulfide.

2. The process as claimed in claim 1, wherein aluminum chloride, AlCl$_3$, is used as the aluminum halide.

3. The process as claimed in claim 1, wherein fluorobenzene or chlorobenzene is used as the halogenobenzene C$_6$H$_5$X.

4. The process as claimed in claim 1, wherein the heating steps are carried out at a temperature of between 70° and 150° C. until the reaction has ended.

5. A process for the preparation of a bis(4-halogenophenyl)phenylphosphine sulfide of the formula

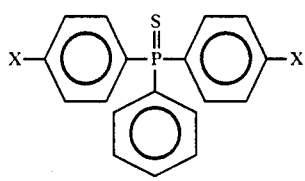

wherein X is F, Cl or Br, comprising heating a reaction mixture of phosphorus thiochoride, an aluminum halide and a halogenobenzene of the formula C$_6$H$_5$X, wherein X has the above-mentioned meaning, in a molar ratio of 1: approximately 1 to 3.5: 2 and then, without isolation of an intermediate, adding to the reaction mixture an approximately one- to ten-fold molar quantity of benzene, relative to the phosphorus thiochloride, and an amount of aluminum halide so that the molar ratio in the reaction mixture of aluminum halide: phosphorus thiochloride converted in the first heating step is 1: approximately 2 to 3.5, and heating the reaction mixture until the reaction is complete to form bis(4-halogenophenyl)-phenylphosphine sulfide.

6. The process as claimed in claim 1 in which the first heating step, the reaction of the phosphorous trichloride, aluminum halide and benzene, is carried out at a temperature of between about 70° and 100° C. for a time between about three and twelve hours.

7. The process as claimed in claim 6 in which the molar ratio of phosphorous trichloride: aluminum halide: benzene in the first heating step is 1: approximately 1 to 2.5: approximately 1.

8. The process as claimed in claim 6 in which the first heating step is carried out in an inert gas atmosphere.

9. The process as claimed in claim 6 in which in the first heating step the reaction mixture is heated under reflux at a temperature between about 70° and 100° C., in the second heating step the reaction mixture is heated under reflux at temperatuers not to exceed about 150° C. for a time of between about five and 20 hours and between the first and second heating steps the reaction mixture is cooled.

10. The process as claimed in claim 6 in which the reaction mixture is cooled after the first heating step and about three to six moles of halogenobenzene is added if the halogenobenzene is fluorobenzene and about six to eight moles if the halogenobenzene is chlorobenzene or bromobenzene and in the second heating step, the reaction mixture is heated under reflux at a temperature not to exceed about 120° C. if the halogenobenzene is fluorobenzene and not to exceed about 150° C. if the halogenobenzene is chlorobenzene or bromobenzene for a time of between about five and 20 hours.

11. The process as claimed in claim 5, wherein aluminum chloride is used as the aluminum halide.

12. The process as claimed in claim 5, wherein fluorobenzene or chlorobenzene is used as the halogenobenzene.

13. The process as claimed in claim 5, wherein the heating steps are carried out at a temperature of between about 70° and 150° C. until the reaction has ended.

14. The process as claimed in claim 5 in which the halogenobenzene is chlorobenzene, bromobenzene or fluorobenzene and the first heating step, the reaction of phosphorus thiochloride, aluminum halide and halogenobenzene, is carried out at a temperature not to exceed about 150° C. if the halogenobenzene is chlorobenzene or bromobenzene and 120° C. if the halogenobenzene is fluorobenzene.

15. The process as claimed in claim 1 in which the first heating step is carried out in an inert gas atmosphere.

16. The process as claimed in claim 14 in which in the first heating step the reaction mixture is heated under reflux for a time between about one and ten hours, the second heating step is heated under reflux for a time between about eight and 20 hours and between the first and second heating steps, the reaction mixture is cooled.

17. The process as claimed in claim 14 in which the reaction mixture is cooled after the first heating step and about three to six moles of benzene is added and in the second heating step, the reaction mixture is heated under reflux for a time between about eight and 20 hours.

* * * * *

UNITED STATES PATENT AND TRADEMARK OFFICE
CERTIFICATE OF CORRECTION

PATENT NO. : 4,670,601

DATED : June 2, 1987

INVENTOR(S) : Hans-Jerg Kleiner et al.

It is certified that error appears in the above-identified patent and that said Letters Patent is hereby corrected as shown below:

Column 10, lines 60 and 64 (Claim 1, lines 5 and 9),

Column 11, line 1 (Claim 1, line 14), line 40 (Claim 6, line 2) and line 45 (Claim 7, line 2), "phosphorous", each occurrence, should read -- phosphorus --.

Column 12, line 3, (Claim 9, line 5), "temperatuers" should read -- temperatures --.

Column 12, line 36, (Claim 15, line 1), "Claim 1" should read -- Claim 14 --.

Column 12, line 48, (Claim 17, line 4), "step," should read -- step --.

Signed and Sealed this

Nineteenth Day of January, 1988

Attest:

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,670,601

DATED : June 2, 1987

INVENTOR(S) : Hans-Jerg Kleiner et al.

It is certified that error appears in the above-identified patent and that said Letters Patent is hereby corrected as shown below:

Column 11, lines 1 and 2, (Claim 1, lines 14 and 15), "aluminum halide:phosphorus trichloride" should read --phosphorus trichloride:aluminum halide--.

Column 11, lines 34 and 35 (Claim 5, lines 13 and 14), "aluminum halide:phosphorus thiochloride" should read --phosphorus thiochloride:aluminum halide--.

Signed and Sealed this

Thirteenth Day of September, 1988

Attest:

DONALD J. QUIGG

*Attesting Officer*  *Commissioner of Patents and Trademarks*